United States Patent [19]

Nelson

[11] Patent Number: 4,507,501

[45] Date of Patent: Mar. 26, 1985

[54] PROCESS FOR PREPARING TERTIARY PHOSPHINES

[75] Inventor: Gunner E. Nelson, Baton Rouge, La.

[73] Assignee: Ethyl Corporation, Richmond, Va.

[21] Appl. No.: 545,463

[22] Filed: Oct. 26, 1983

[51] Int. Cl.$^3$ .............................................. C07F 9/50
[52] U.S. Cl. ......................................... 568/17; 568/8
[58] Field of Search ..................................... 568/8, 17

[56] References Cited

U.S. PATENT DOCUMENTS 3,261,871  7/1966  Fritzsche et al. .
3,280,195 10/1966  Fritzsche et al. .
3,847,999 11/1974  Gardner et al. .
4,008,282  2/1977  Townsend et al. .
4,113,783  9/1978  Malpass et al. .
4,131,624 12/1978  Davis et al. .

OTHER PUBLICATIONS

Chemical Abstracts 53 9879c (1959).
Chemical Abstracts 61 8335f (1964).
Chemical Abstracts 63 8398h (1966).
Kosolapoff et al., Organic Phosphorus Compounds, Wiley-Intersc. Pub. N.Y., vol. 1, pp. 45–47 (1972).

Primary Examiner—Helen M. S. Sneed
Attorney, Agent, or Firm—Donald L. Johnson; John F. Sieberth; Patricia J. Hogan

[57] ABSTRACT

A tertiary phosphine oxide, such as triphenylphosphine oxide, is reduced to the corresponding tertiary phosphine in the presence of a sodium aluminum hydride/aluminum chloride reducing agent.

4 Claims, No Drawings

PROCESS FOR PREPARING TERTIARY PHOSPHINES

Field of Invention

This invention relates to a process for preparing tertiary phosphines and more particularly relates to such a process wherein a tertiary phosphine oxide is reduced to the corresponding tertiary phosphine.

BACKGROUND

It is known that tertiary phosphines are synthesizable by various techniques, including the reduction of tertiary phosphine oxides. The tertiary phosphine oxide reduction processes that have been used in the past have included the processes of U.S. Pat. Nos. 3,261,871 (Fritzche et al. I), 3,280,195 (Fritzche et al. II), 3,847,999 (Gardner et al.), 4,008,282 (Townsend et al.), 4,113,783 (Malpass et al.), and 4,131,624 (Davis et al.); Issleib et al., CA 53:9879c; Fritzche et al. III, CA 61:8335f; Koester et al., CA 63: 8398h; and G. M. Kosolapoff et al., *Organic Phosphorus Compounds*, Vol. 1, Wiley Interscience Publishers (New York), 1972, pp. 45–47, as well as processes wherein the oxide has been converted to the tertiary phosphine via an intermediate. One of these processes, a process of Issleib et al., involves reducing triphenylphosphine oxide with aluminum hydride in ether.

Some of these processes have achieved some measure of success as commercially feasible techniques, but there is still a need for an economical, efficient method of reducing tertiary phosphine oxides to the corresponding phosphines.

SUMMARY OF THE INVENTION

An object of this invention is to provide a novel process for reducing tertiary phosphine oxides to the corresponding phosphines.

Another object is to provide such a process which results in a high yield of tertiary phosphine.

These and other objects are attained by reducing a tertiary phosphine oxide in the presence of a sodium aluminum hydride/aluminum chloride reducing agent.

DETAILED DESCRIPTION

Tertiary phosphine oxides utilizable in the practice of the invention are compounds corresponding to the formula:

RR'R"PO wherein R, R', and R" are independently selected from organic groups containing about 1–20 carbons. Generally the organic groups are hydrocarbon groups, e.g., alkyl, cycloalkyl, aryl, alkaryl, or aralkyl groups; and the invention is particularly useful for reducing tertiary aromatic phosphine oxides, such as triphenylphosphine oxide, tritolylphosphine oxide, etc., to the corresponding phosphines.

The reducing agent of the invention is a combination of sodium aluminum hydride and aluminum chloride in a mol ratio of about 3/1. In the course of the reaction, this reducing agent is believed to generate aluminum hydride in situ to provide 4 mols of aluminum hydride per mol of aluminum chloride. This component of the reaction mixture is employed in an effective amount which varies with the temperature employed. For example, the amount is generally such as to provide about 0.25 mol of aluminum chloride per mol of triphenylphosphine oxide when ambient temperatures are utilized, and the amount is generally less when higher temperatures are used.

The reaction is preferably conducted in the presence of a suitable solvent, such as dimethoxyethane, tetrahydrofuran, etc., which is used in diluent amounts.

The temperatures employed for the reaction are temperatures effective for reduction with the sodium aluminum hydride/aluminum chloride reducing agent, generally temperatures in the range of about 20°–50° C. Temperatures in the room temperature area are apt to be more convenient, but higher temperatures can speed the reaction and improve its stoichiometry.

The following example is given to illustrate the invention and is not intended as a limitation thereof.

EXAMPLE

A suitable reaction vessel was charged with a solution of 10 mmols of triphenylphosphine oxide in a mixture of 25 ml of toluene and 15 ml of dimethoxyethane and then with 2.5 mmols of aluminum chloride. Then 7.5 mmols of sodium aluminum hydride were added as an 8% solution in dimethoxyethane, and the mixture was stirred at 25° C. with samples being taken periodically for GLC analysis. After three hours, the analysis showed a triphenylphosphine/triphenylphosphine oxide area ratio of 64/36, which was increased to 77/23 after the reaction mixture had been stirred overnight.

It is obvious that many variations can be made in the products and processes set forth above without departing from the spirit and scope of this invention.

I claim:

1. A process which comprises reacting a tertiary phosphine oxide with a sodium aluminum hydride/aluminum chloride reducing agent so as to form the corresponding tertiary phosphine.

2. The process of claim 1 wherein the tertiary phosphine oxide is triphenylphosphine oxide.

3. The process of claim 1 wherein the sodium aluminum hydride and aluminum chloride are employed in a mol ratio of about 3/1.

4. The process of claim 1 wherein the reduction is conducted at a temperature in the range of about 20°–50° C.

* * * * *